United States Patent [19]

Carson et al.

[11] 4,111,954

[45] Sep. 5, 1978

[54] PREPARATION OF 1-METHYLPYRROLE-2-ACETONITRILE

[75] Inventors: John Robert Carson, Norristown; Richard J. Carmosin, Philadelphia; Anthony T. Stefanski, Fort Washington, all of Pa.

[73] Assignee: McNeil Laboratories, Incorporated, Fort Washington, Pa.

[21] Appl. No.: 789,309

[22] Filed: Apr. 20, 1977

[51] Int. Cl.$^2$ ............................................ C07D 207/34
[52] U.S. Cl. ................................................ 260/326.62
[58] Field of Search ..................................... 260/326.62

[56] References Cited

FOREIGN PATENT DOCUMENTS 1,198,828  7/1970  United Kingdom ................ 260/326.62

OTHER PUBLICATIONS

Kirk–Othmer "Encyclopedia of Chemical Technology", vol. 19, p. 377 (1969).
Brotherton et al., "Chem. Rev.", p. 875, vol. 59, (1959).

*Primary Examiner*—Donald G. Daus
*Assistant Examiner*—David B. Springer
*Attorney, Agent, or Firm*—Salvatore R. Conte

[57] ABSTRACT

1-Methylpyrrole-2-acetonitrile is prepared by the reduction of α-imino-1-loweralkylpyrrole-2-acetonitrile using hydrogen sulfide as the reducing agent.

6 Claims, No Drawings

PREPARATION OF 1-METHYLPYRROLE-2-ACETONITRILE

DESCRIPTION OF THE PREFERRED EMBODIMENT

This invention relates to a novel process of preparing 1-loweralkylpyrrole-2-acetonitrile of the formula:

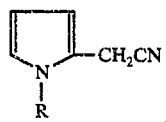

wherein R is loweralkyl, preferably methyl.

As used herein, "loweralkyl" refers to straight or branch chained alkyls having from 1 to 5 carbon atoms, for example, methyl, ethyl, propyl, isopropyl, butyl, tert-butyl, pentyl and the like.

According to the instant process, an α-imino-1-loweralkylpyrrole-2-acetonitrile of formula (II) is reduced to the corresponding 1-loweralkylpyrrole-2-acetonitrile of formula (I) by the action of hydrogen sulfide as the reducing agent.

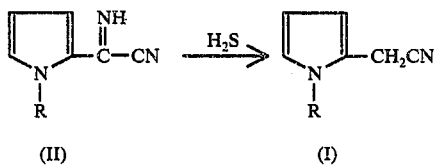

Suitable inert organic solvents which may be utilized for the reduction reaction are aromatic hydrocarbons such as, for example, benzene, toluene, xylene and the like; halocarbons such as, for example, methylene dichloride, chloroform and the like; amines such as, for example, pyridine, triethylamine, triethanolamine and the like; lower alkanols, such as, for example, methanol, ethanol, methoxyethanol and the like; and dipolar aprotic organic solvents such as, for example, dimethyl sulfoxide (DMSO), N,N-dimethylformamide (DMF), ethyl acetate, acetonitrile and the like.

The reduction reaction may be performed at reaction temperatures varying from about −20° C to about 50° C, preferably 0° to 25° C, and atmospheric pressure to about 60 p.s.i. pressure may be advantageously employed.

1-Methylpyrrole-2-acetonitrile (I) has been reported in the literature as being a useful intermediate in the preparation of 5-aroyl-pyrrole-2-acetic acid derivatives having anti-inflammatory activity (e.g., see U.S. Pat. No. 3,752,826).

The α-imino-acetonitriles of formula (II), wherein R is loweralkyl, may be prepared by the interaction of N-loweralkylpyrrole (III) and cyanogen (IV) in the presence of hydrogen chloride under Houben Hoesch reaction conditions. In general, dry HCl gas is bubbled through a solution of (III) and (IV) in an inert organic solvent suitable for Houben Hoesch reactions, e.g., an aprotic organic solvent such as, ethers, halogenated hydrocarbons, aromatic hydrocarbons and the like. Alternatively, an ethereal solution of HCl is slowly added to the solution of (III) and (IV). The resultant α-imino-1-loweralkylpyrrole-2-acetonitrile HCl salt (V) is transformed to the corresponding free imino state (II) by treatment with at least an equivalent amount of a suitable acid-neutralizing base, e.g., an alkali metal carbonate of bicarbonate, or a liquid amine which can serve as halogen acid acceptor such as pyridine, triethylamine and the like.

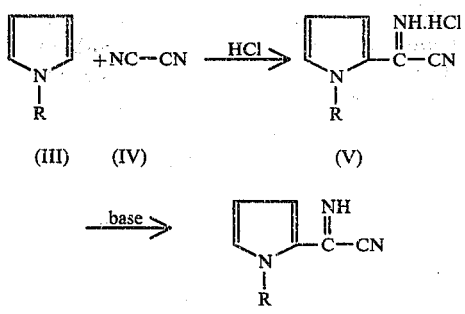

The following examples are intended to illustrate and not to limit the scope of the present invention. Unless otherwise stated, all parts therein are by weight.

EXAMPLE I

N-methylpyrrole-2-acetonitrile

N-methylpyrrole (4 g, 0.049 mole) is dissolved in 40 ml of dry (ethanol-free) chloroform in a dry, 200 ml, 3-necked round-bottomed flask and flushed with a stream of dry nitrogen. The temperature of the solution is lowered to 0° C and cyanogen (3.25 g, 0.063 mole) is added. Hydrogen chloride (dried through sulfuric acid) is introduced in a slow steady stream with mechanical stirring at 0° C for 4 hrs at which time all the N-methylpyrrole has been consumed. The hydrogen chloride flow is stopped; the chloroform is evaporated to ½ its volume at reduced pressure and room temperature; and the temperature is then lowered to −40° C. Dry pyridine (25 ml) is added dropwise with rapid stirring. The rest of the chloroform is evaporated at reduced pressure and then 25 mls of additional pyridine is added. The reaction mixture is allowed to warm to room temperature and hydrogen sulfide is introduced in a slow stream for 20 minutes. Chloroform (200 ml) is added and the reaction solution is washed with 35% aqueous potassium carbonate solution, followed by a 3N hydrochloric acid wash which is backwashed with chloroform. The combined chloroform extracts are washed with 5% aqueous sodium bicarbonate solution and dried over anhydrous MgSO₄ powder. The mixture is filtered and the filtrate evaporated in vacuo to a brown oil. The oil is distilled under high vacuum to give 840 mg of N-methylpyrrole-2-acetonitrile, bp 61°–65° C at 0.04 Torr.

EXAMPLE II

By repeating the procedure of Example I, except that an equivalent quantity each of N-ethylpyrrole and N-n-butyl-pyrrole is substituted for the N-methylpyrrole utilized therein, the following respective products are obtained:
N-ethylpyrrole-2-acetonitrile; and
N-n-butylpyrrole-2-acetonitrile.

EXAMPLE III

N-methylpyrrole-2-acetonitrile

N-methylpyrrole (2 g, 24.68 mmol) is dissolved in 10 ml of anhydrous ether in a 25 ml, 3-necked, round-bottom flask under nitrogen. The solution temperature is lowered to −20° C and cyanogen (1.8 g, 34.6 mmol) is bubbled in, followed by 3.2 g of dry hydrogen chloride (88 mmol). The reaction is allowed to warm to 0° C, and then kept at this temperature in an ice bath for 2.5 hrs. The ether is evaporated at reduced pressure, and 10 ml of dry pyridine is added to the oil residue. Hydrogen sulfide is introduced in a slow stream with gradual warming to room temperature. The ether is evaporated off in vacuo and the oil residue dissolved in methanol. Analysis of the alcohol solution by thin layer chromatography showed a spot whose $R_f$ matched an authentic sample of N-methylpyrrole-2-acetonitrile, and whose visualization both by U.V. and iodine staining are the same.

We claim:

1. A process of preparing 1-loweralkyl- pyrrole-2-acetonitrile which comprises the step of reducing α-imino-1-loweralkylpyrrole-2-acetonitrile by the action of hydrogen sulfide as the reducing agent in an inert organic solvent at a temperature from about −20° to about 50° C and a pressure from atmospheric pressure to about 60 p.s.i. pressure.

2. A process of preparing 1-methylpyrrole-2-acetonitrile which comprises the step of reducing α-imino-1-methylpyrrole-2-acetonitrile by the action of hydrogen sulfide as the reducing agent in an inert organic solvent at a temperature from about −20° to about 50° C and a pressure from atmospheric pressure to about 60 p.s.i. pressure.

3. A process of preparing 1-loweralkylpyrrole-2-acetonitrile which comprises the steps of interactinhg N-loweralkylpyrrole and cyanogen in the presence of hydrogen chloride in an inert organic solvent to form an α-imino-1-loweralkylpyrrole-2-acetonitrile HCl salt, treating the latter salt with at least an equivalent amount of an acid-neutralizing base, and reducing the thus-obtained α-imino-1-loweralkylpyrrole-2-acetonitrile to said 1-loweralkylpyrrole-2-acetonitrile by the action of hydrogen sulfide as the reducing agent in an inert organic solvent at a temperature from about −20° to about 50° C and a pressure from atmospheric pressure to about 60 p.s.i. pressure.

4. A process of preparing 1-methylpyrrole-2-acetonitrile which comprised the steps of interacting N-methylpyrrole and cyanogen in the presence of hydrogen chloride in an inert organic solvent to form an α-imino-1-methypyrrole-2-acetonitrile HCl salt, treating the latter salt with at least an equivalent amount of an acid-neutralizing base, and reducing the thus-obtained α-imino-1-methylpyrrole-2-acetonitrile to said 1-methylpyrrole-2-acetonitrile by the action of hydrogen sulfide as the reducing agent in an inert organic solvent at a temperature from about −20° to about 50° C and a pressure from atmospheric pressure to about 60 p.s.i. pressure.

5. The process of claim 2 wherein said temperature is from 0° to 25° C.

6. The process of claim 4 wherein said temperature is from 0° to 25° C.

* * * * *